US012806133B2

(12) United States Patent
Oger et al.

(10) Patent No.: US 12,806,133 B2
(45) Date of Patent: *Nov. 24, 2026

(54) METHOD FOR OBTAINING AQUEOUS EXTRACTS OF TEA LEAVES, COMPOSITIONS COMPRISING SUCH EXTRACTS AND COSMETIC USES THEREOF

(71) Applicant: ISP INVESTMENTS LLC, Wilmington, DE (US)

(72) Inventors: Elodie Oger, Antibes (FR); Laura Mouret, Biot (FR)

(73) Assignee: ISP INVESTMENTS LLC, Wilmington, DE (US)

(*) Notice: Subject to any disclaimer, the term of this patent is extended or adjusted under 35 U.S.C. 154(b) by 679 days.

This patent is subject to a terminal disclaimer.

(21) Appl. No.: 18/035,711

(22) PCT Filed: Nov. 23, 2021

(86) PCT No.: PCT/EP2021/082631

§ 371 (c)(1),
(2) Date: May 5, 2023

(87) PCT Pub. No.: WO2022/106718

PCT Pub. Date: May 27, 2022

(65) Prior Publication Data

US 2024/0009111 A1 Jan. 11, 2024

(30) Foreign Application Priority Data

Nov. 23, 2020 (FR) ....................................... 2012019

(51) Int. Cl.

| | |
|---|---|
| ***A61K 8/9789*** | (2017.01) |
| ***A61K 8/55*** | (2006.01) |
| ***A61K 8/81*** | (2006.01) |
| ***A61Q 19/00*** | (2006.01) |
| ***A61Q 19/08*** | (2006.01) |

(52) U.S. Cl.

CPC .............. *A61K 8/9789* (2017.08); *A61K 8/55* (2013.01); *A61K 8/8176* (2013.01); *A61Q 19/007* (2013.01); *A61Q 19/08* (2013.01); *A61K 2800/412* (2013.01); *A61K 2800/805* (2013.01)

(58) Field of Classification Search

None

See application file for complete search history.

(56) References Cited

U.S. PATENT DOCUMENTS

2010/0119463 A1 5/2010 Jacobs

FOREIGN PATENT DOCUMENTS

| | | | |
|---|---|---|---|
| CN | 105194102 | A | 12/2015 |
| CN | 103690434 | B | 3/2016 |
| CN | 105770192 | A | 7/2016 |
| CN | 106074295 | A | 11/2016 |
| CN | 109567164 | A | 4/2019 |
| DE | 19820629 | A1 | 11/1999 |
| DE | 19824727 | A1 | 12/1999 |
| EP | 0995427 | A2 | 4/2000 |
| EP | 1932513 | A2 | 6/2008 |
| FR | 2953406 | B1 | 3/2012 |
| JP | 2004-159597 | A2 | 6/2004 |
| JP | 2006-191924 | A2 | 7/2006 |
| JP | 2015-130841 | A2 | 7/2015 |
| KR | 1196440 | B1 | 11/2012 |
| KR | 10-2016-0021734 | A | 2/2016 |
| KR | 10-2016-0085028 | A | 7/2016 |
| KR | 10-2018-0026001 | A | 3/2018 |
| KR | 10-2018-0026923 | A | 3/2018 |
| KR | 10-2018-0125828 | A | 11/2018 |
| KR | 10-2019-0124579 | A | 11/2019 |
| WO | WO 0045769 | A2 | 8/2000 |
| WO | WO2003009825 | A3 | 4/2003 |
| WO | WO2006111666 | A1 | 10/2006 |
| WO | WO 2009063068 | A1 | 5/2009 |
| WO | WO2019208956 | A1 | 10/2019 |
| WO | WO 2020089831 | A1 | 5/2020 |
| WO | 2021/156104 | A1 | 8/2021 |

OTHER PUBLICATIONS

International Search Report of PCT/EP2021/082631 filed pm Nov. 23, 2021.

Abrutyn E, "Chelating Agents", COSMETICS & Toiletries Magazine, Allured Publishing Corp, US,vol. 126, No. 8, Aug. 1, 2011 (Aug. 1, 2011), p. 542, 544-546, XP007919732, ISSN:0361-4387 1-13 p. 544, colonne de droite.

(Continued)

*Primary Examiner* — David J Blanchard
*Assistant Examiner* — Kaeleigh E Olsen
(74) *Attorney, Agent, or Firm* — Aseem Mehta; Nathalie Tietcheu

(57) ABSTRACT

The invention relates to a process for obtaining aqueous extracts of tea leaves (*Camellia sinensis*), in particular of leaves of fresh tea, pu'er tea, matcha tea or green tea. The invention also relates to tea extracts enriched with small RNAs, sugars, phenolic compounds, organic acids, theine and theanine, as well as to cosmetic compositions comprising such extracts and their cosmetic uses for the care of the skin, the scalp, and the appendages and more particularly for protecting the skin from external aggressions and oxidation, combating the signs of skin ageing, increasing photoprotection, lightening the skin and improving skin hydration.

8 Claims, 3 Drawing Sheets

(56) References Cited

OTHER PUBLICATIONS

"Pu'er tea gel used for preventing and treating atopic dermatitis, is prepared using pu'er tea extract, matrix, humectant, co-Solvent, preservative, and distilled water", Database WPI Thomson Scientific, London, GB; Aug. 1, 2016 (Aug. 1, 2016), vol. 2016, No. 83, AN 2016-48336W.

Pingjing Zhang et al, "Use of small RNA as antiaging cosmeceuticals", United States Nov. 1, 2013 (Nov. 1, 2013), p. 455-468, Retrouvé de : URL:http://journal.scconline.org//pdf/cc2013/cc064n06/p00455-p00468.pdf XP055282728 [Extrait le Jul. 26, 2019] 1-13 abrégé tableau 1 Small RNA in antiwrinkle cosmeceuticals;p. 459.

[Fig. 1]
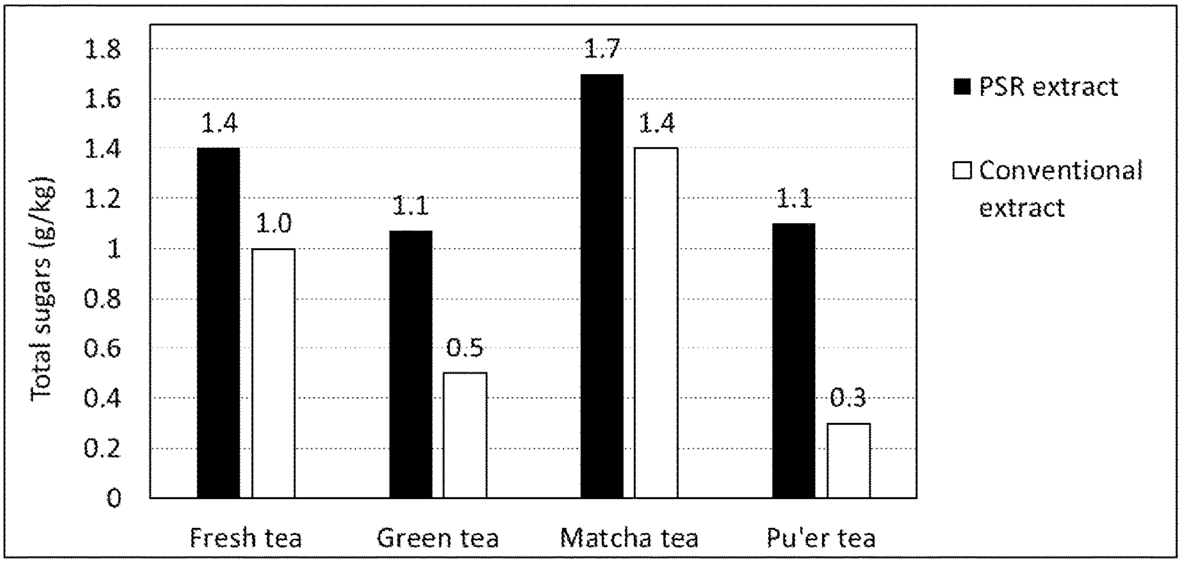
[Fig. 2]
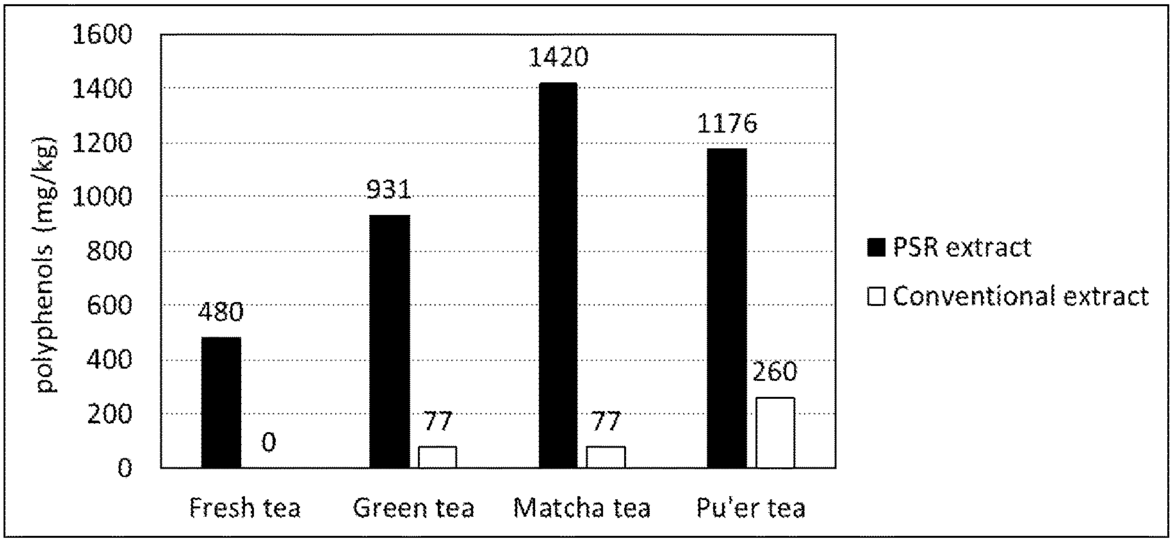

[Fig. 3]
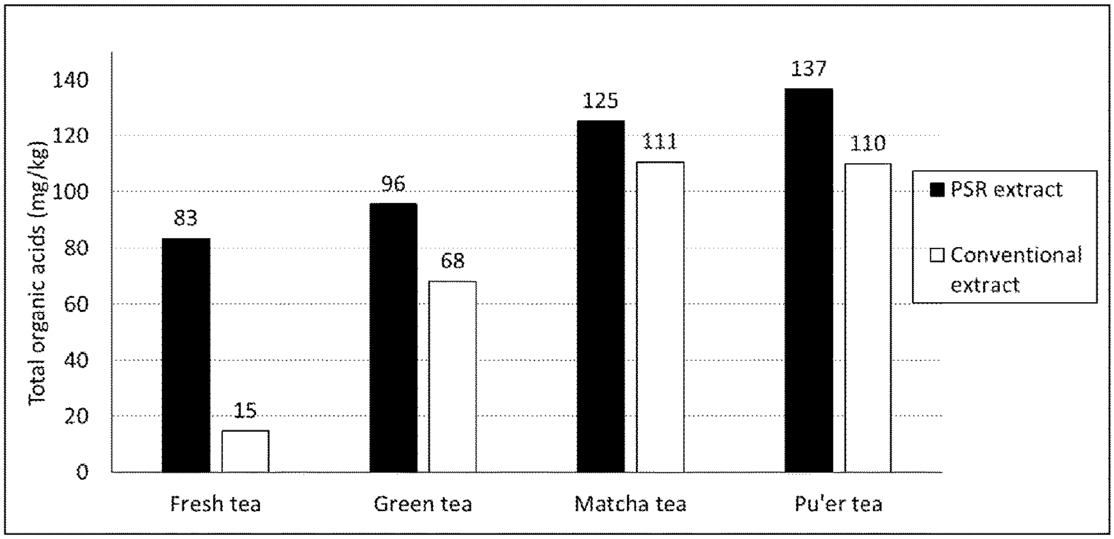
[Fig. 4]
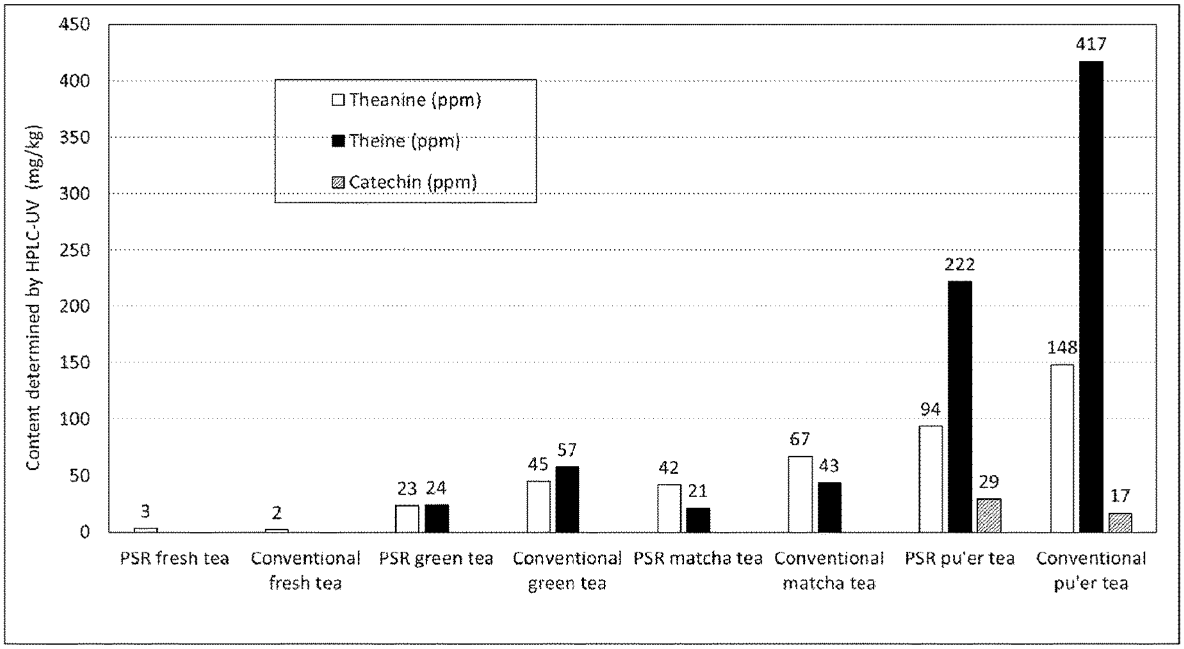

[Fig. 5]
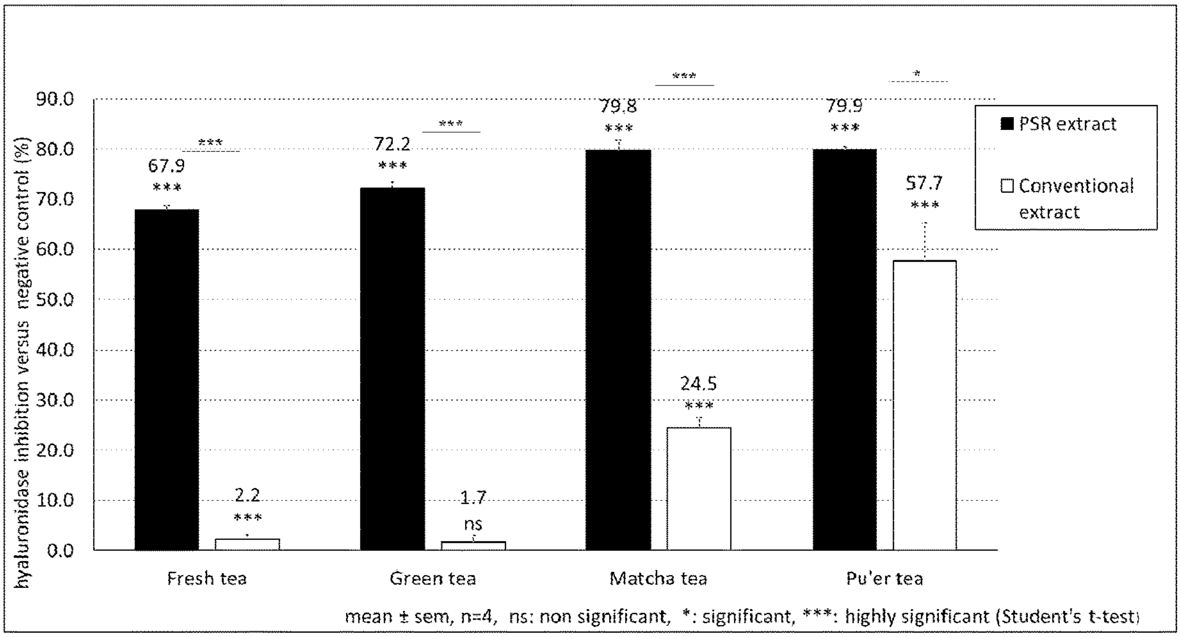
[Fig. 6]
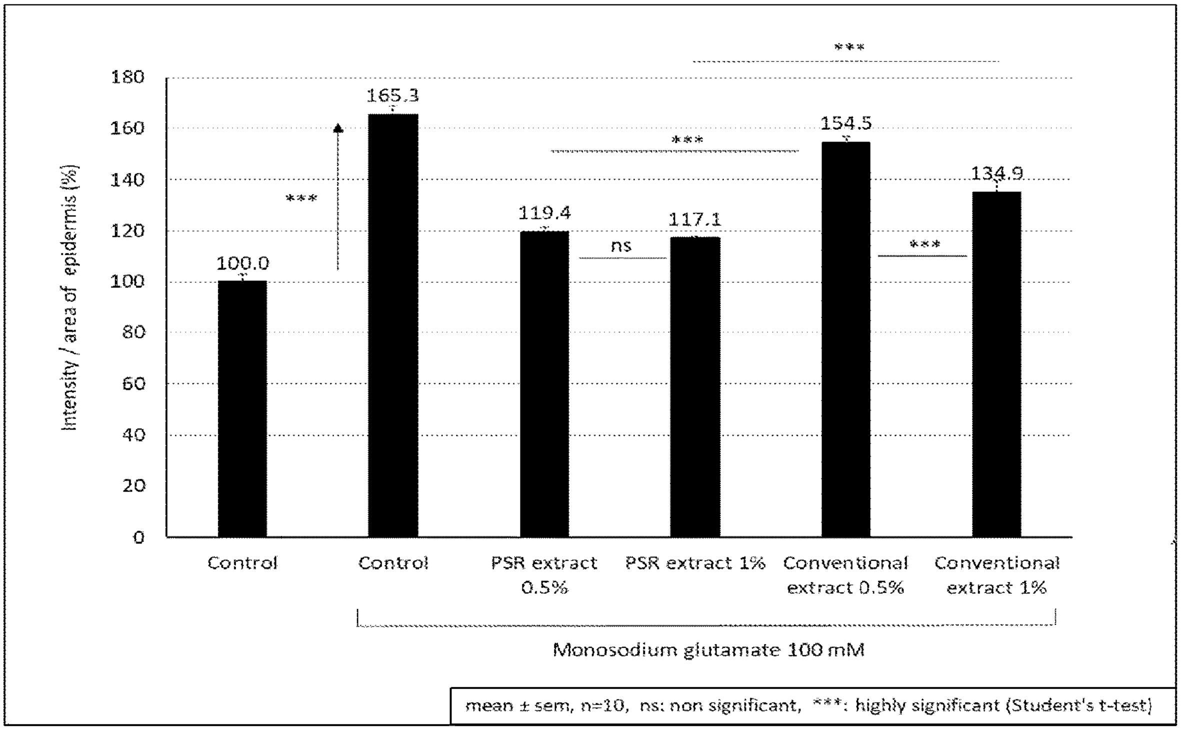

METHOD FOR OBTAINING AQUEOUS EXTRACTS OF TEA LEAVES, COMPOSITIONS COMPRISING SUCH EXTRACTS AND COSMETIC USES THEREOF

TECHNICAL FIELD

The invention relates to the field of cosmetics and more particularly to active ingredients of natural origin used in the preparation of cosmetic formulations to improve the appearance of the skin or protect it.

The invention relates to a process for obtaining aqueous extracts of different types of tea, in particular fresh tea, pu'er tea, matcha tea or green tea, as well as tea extracts enriched with small RNAs, with sugars, with phenolic compounds, with organic acids, with theine and with theanine, the cosmetic compositions comprising such extracts and their cosmetic uses for the care of the skin, the scalp and the appendages and more particularly for protecting the skin from external aggressions and oxidation, combating the signs of skin ageing, increasing photoprotection, lightening the skin and improving skin hydration.

TECHNICAL BACKGROUND OF THE INVENTION

Plants of the genus *Camellia* comprise a large number of different species belonging to the Theaceae family. Botanists estimate that there are between 100 and 250 species of plants belonging to this genus. The genus *Camellia* is native to eastern and southern Asia from the Himalayan range, to Japan and Indonesia.

Among the best known and most used species is the species *Camellia sinensis*, commonly known as the tea plant, which itself includes three botanical varieties: *Camellia sinensis* var. *assamica, Camellia sinensis* var. *sinensis* (Yunnan) and *Camellia sinensis* var. *Cambodiensis*. Another species, *Camellia assamica*, is known as a tea plant but its more delicate cultivation limits its use.

The species *Camellia sinensis* is used in the food industry for the production of various teas using the leaves. The processing of the leaves of *Camellia sinensis* combined with the growing conditions will give the tea its distinctive features. Teas are differentiated in particular by their colour and their organoleptic characteristics.

Once harvested, the leaves undergo a treatment which is specific to the type of tea and which determines the final degree of oxidation of the leaves. The different key steps are withering (softening of the tea leaves in order to dry them), rolling (to extract the essential oils), fixing (by heating in order to stop oxidation of the leaves), drying (hot air flow in order to lower the humidity level) and fermentation (the leaves are placed in an oxygen-poor environment in order to accelerate the proliferation of micro-organisms).

Green tea is defined in the present application as a tea (*Camellia sinensis*) of which the natural oxidation is stopped rapidly after the leaves are picked. In order to obtain green tea, the tea leaves are withered, rolled to extract the juices and then heated to block the oxidation process. There are two possible heating methods: the Chinese method, which uses copper basins placed on a fire, or the Japanese method, which passes the leaves through steam jets (thus preserving their properties). Blocking oxidation maximises the content of molecules of interest such as catechin and theanine.

Matcha tea is defined in the present application as a green tea from Japan that has been obtained from tea leaves (*Camellia sinensis*) reduced to powder (matcha means "tea powder"). In order to obtain matcha tea, the producers practice cultivation in a shaded area in order to slow down photosynthesis and thus the transformation of theanine into tannins. This technique gives matcha tea a unique fruity and vegetable flavour. The leaves are steamed to stop oxidation and obtain a green tea. Once dried, the leaves are crushed with a stone grinder to obtain a very fine bright green powder. Matcha tea is very rich in polyphenols, a class of antioxidants with recognised health benefits.

Pu'er tea is defined in this application as post-fermented green tea, also called sheng pu'er in Asia or raw pu'er in the West. pu'er tea is native to the Yunnan region of China. It is made from leaves of the species *Camellia sinensis* var. *assamica*. The tea leaves undergo a first oxidation at the place of production before being pressed into cakes or bricks. The cakes then undergo a moderate fermentation by means of micro-organisms, which can be accelerated in a humid environment. Subsequently, the tea cakes are partially oxidised during the natural ageing process.

Numerous extracts of tea leaves are described in the literature, in part for their richness in phenolic compounds, often catechin-type polyphenols. On the other hand, there are few extracts on the market or described in the prior art that claim a composition rich in different types of phytomolecules other than polyphenols. Indeed, most of the tea leaf extraction methods in the prior art describe processes using organic solvents for their abilities to extract polyphenols and mainly catechin-type polyphenols (WO2006/111666, KR2016021734A, KR2018125828A). The described extracts are rich in polyphenols and flavonoids, but do not contain phenolic molecules of the phenolic acid type because these are not extracted by this type of technique. Indeed, phenolic acids are mainly extracted in a polar solvent and ideally with water. Also, other phytocompounds, which are known for their beneficial effects such as amino acids, organic acids, proteins, sugars and oligo-ribonucleotides such as small RNAs are not optimally extracted by these methods.

Users of cosmetic products now wish to use formulas that are as natural as possible and that are just as effective as or even more effective than synthetic products. In the present invention the extracts made are 100% natural in order to meet the requirements of the consumers.

Moreover, despite the numerous anti-ageing cosmetic products already on the market, the need for new effective cosmetic ingredients of natural origin is growing.

One problem that the invention proposes to solve is to provide new aqueous tea extracts that meet the requirements of the current cosmetic market with respect to naturalness criteria and that nevertheless have remarkable biological efficacy, as well as an absence of toxicity.

Indeed, too high a concentration of phenolic compounds such as catechin may cause phototoxicity phenomena and may limit the stability of the extract over time. The extracts described in the present invention have a concentration of polyphenols and other phytomolecules of interest consistent with good efficacy. They also have a significant stability over time and a lack of toxicity.

Another problem that the invention proposes to solve is to provide new aqueous tea extracts enriched with compounds known to be effective on the skin, such as sugars, phenolic compounds, organic acids, theine and theanine, as well as small RNAs obtained by the process.

The inventors have developed new tea extracts specifically enriched with small RNAs, sugars, phenolic and organic compounds, organic acids, theine, theanine, by a process that does not present the disadvantages of the prior art processes, such as the use of detergents and solvents potentially toxic in cosmetics.

The extracts thus obtained can be used in cosmetics for the care of the skin, scalp and appendages, to obtain multiple benefits and more particularly to protect the skin from external aggression and oxidation, to fight against the signs of skin ageing, to increase photoprotection, to lighten the skin, to improve skin hydration, to reinforce the barrier function or even soothe the skin.

SUMMARY OF THE INVENTION

The invention firstly relates to a process for obtaining an aqueous extract of tea leaves, of the species *Camellia sinensis*, selected from fresh tea, pu'er tea, matcha tea or green tea, comprising the following steps:

a) bringing the tea leaves or tea powder into contact with water, and then possibly crushing them;
b) adding phytic acid;
c) adjusting the pH to a value between 10 and 11;
d) keeping the mixture under agitation for at least one hour at a temperature between 40 and 80° C.;
e) purifying the mixture obtained in c) to eliminate the residual solid plant material and collect the filtrate;
f) adjusting the pH to a value between 6 and 8;
g) treating the mixture with powdered activated charcoal.
h) filtering to remove the activated charcoal and collecting the filtrate;
i) treating the filtrate with polyvinylpolypyrrolidones (PVPP);
j) filtering to remove the polyvinylpolypyrrolidones and collecting the filtrate;
k) checking and readjusting the pH of the filtrate, if necessary, to a value between 6 and 6.5.

The invention secondly relates to an aqueous crude extract of fresh tea leaves, pu'er tea, matcha tea or green tea, enriched with small RNAs of a length of at most 150 nucleotides, with sugars, with phenolic compounds and with organic acids, free of DNA, obtainable by the process of the invention, having a dry weight of 5 to 30 g/kg, and comprising from 0.5 to 10 g/kg of sugars, from 0.050 to 2 g/kg of organic acids, from 0.050 to g/kg of phenolic compounds including 0 to 200 mg/kg of catechin, 0.020 to 2 g/kg of theine and 0.020 to 2 g/kg of theanine, and 50 to 350 mg/kg of low molecular weight RNA of a length of at most 150 nucleotides.

The invention also relates to a diluted aqueous extract of fresh tea leaves, pu'er tea, matcha tea or green tea, enriched with small RNAs of a length of at most 150 nucleotides, with sugars, with phenolic compounds and with organic acids, free of DNA, obtainable by the process of the invention, having a dry weight between 4 and 20 g/kg dry weight, a concentration of 0.2 to 5 g/kg of sugars, 0.030 to 1 g/kg of organic acids, 0.030 to 3 g/kg of phenolic compounds including 0 to 120 mg/kg of catechin, 0.010 to 1 g/kg of theine and to 1 g/kg of theanine, and 10 to 250 mg/kg of low molecular weight RNA of a length of at most 150 nucleotides, by weight of the total weight of the extract.

The invention thirdly relates to a composition comprising, as an active ingredient, an effective amount of at least one diluted aqueous extract of tea leaves selected from an extract of fresh tea, pu'er tea, matcha tea or green tea according to the invention, or any mixture thereof, and a physiologically acceptable medium.

The invention relates fourthly to the cosmetic use of the composition according to the invention for the care of the skin, the scalp and the appendages, and more particularly to protect the skin from external aggression and oxidation, to fight against the signs of skin ageing, to increase photoprotection, to lighten the skin, and to improve skin hydration.

BRIEF DESCRIPTION OF THE DRAWINGS

The invention and the advantages thereof will be better understood upon reading the following description and non-limiting embodiments, illustrated with respect to the appended figures in which:

FIG. 1 Shows an evaluation of the total sugar content by colorimetric method in the different tea extracts obtained according to Examples 1 and 2.

FIG. 2 Shows an evaluation of the polyphenol content by colorimetric method in the different tea extracts obtained according to Examples 1 and 2.

FIG. 3 Shows an evaluation of the organic acid content by HPLC-MS in the different tea extracts obtained according to Examples 1 and 2.

FIG. 4 Shows an evaluation of theanine, theine and catechin content by HPLC-UV in the different tea extracts obtained according to Examples 1 and 2.

FIG. 5 Shows an evaluation of the hyaluronidase inhibition of the different tea extracts obtained according to Examples 1 and 2 by measuring turbidity.

FIG. 6 Shows an evaluation of reactive oxygen species levels in skin biopsies stressed by monosodium glutamate and treated with the different pu'er tea extracts obtained according to Examples 1 and 2.

DETAILED DESCRIPTION OF THE INVENTION

Definitions

All terms used in the present description have the most widely known meaning unless otherwise stated. For the purposes of the invention the following terms are defined as follows:

The term "tea extract" means all types of treatment of leaves of the species *Camellia sinensis.*

The term "tea" means the leaves of the species *Camellia sinensis* in all their forms; whole or powdered, dry or fresh.

The terms "small RNAs" or "RNAs of low molecular weight", or "small RNAs of a length of at most 150 nucleotides" means non-coding RNAs (ribonucleic acids) of low molecular weight, of a length of at most 150 nucleotides, such as all types of small non-messenger RNAs, single and/or double stranded, for example microRNAs, interfering RNAs, introns, small nuclear RNAs or even any fragment of RNA from the plant and extracted by the process described in the invention. In the extracts according to the invention, the small RNAs are in the form of a complex mixture of numerous RNAs with a size predominantly between and 150 nucleotides. Thus, the RNAs resulting from syntheses and thus not natural do not feature in this definition.

The term "organic acids" means α-hydroxy acids (or AHAs), i.e. carboxylic acids derived from sugars contained in tea leaves, such as lactic, malic, citric, tartaric, succinic and uronic acids.

"Phenolic compounds" mean molecules of plant origin which have at least one aromatic ring of the phenolic type bearing one or more hydroxyl groups, such as phenolic acids, flavonoids such as catechin or its derivatives, tannins or any other polyphenol. Phenolic compounds are known to be powerful antioxidant molecules, both in the plant and for cosmetic use. These secondary plant metabolites are also produced in the defence mechanisms of the plant by biotic or abiotic stresses.

The term "sugars" means all types of sugars present in plants, such as monosaccharides like glucose, fructose as well as oligo and polysaccharides. Generally, polysaccharides contain more than ten monosaccharide units, while oligosaccharides contain three to ten monosaccharide units.

The term "phytomolecules of interest" means all the molecules present in the tea extracts of the invention and, in particular, small RNAs of a length of at most 150 nucleotides, sugars, phenolic compounds, organic acids, theine and theanine.

When a range of values is described, the bounds of that range should be understood as explicitly including all intermediate values in the range. For example, a range of values between 1% and 10% should be understood to include 1%, 2%, 3%, 4%, 5%, 6%, 7%, 8%, 9%, and 10%, as well as all decimal values between 1% and 10%.

Numerical percentage values are percentages by weight, i.e., the weight of a compound relative to the total weight of the intended mixture, unless otherwise specified.

The compositions described herein may "comprise", "consist of" or "consist substantially of" the essential compounds or optional ingredients.

The expression "consist substantially of" means that the composition or component may include additional ingredients, but only if the additional ingredients do not alter the basic or novel features of the composition or of the use described in the present application.

The term "topical application" means applying or spreading the extract according to the invention, or a composition containing it, on the surface of the skin or a mucous membrane.

The term "skin" refers to the skin of the face, in particular the eye area and the mouth, the nose, the forehead, the neck, the hands, but also the skin of the entire body.

The term "scalp" refers to the skin covering the skull, including the hair follicles and interfollicular skin spaces.

The term "appendages" refers to hair on the head and body hair (produced by hair follicles), as well as nails, which are rich in keratin.

The expression "lighten the skin" means reducing the intensity of the skin colour linked to the melanin content of the epidermis, either homogeneously or in a localised manner by acting on pigmentary disorders, such as age spots or senile lentigos.

The term "effective amount" means the minimum amount of extract according to the invention that is necessary to obtain at least one of the desired biological activities or to protect the skin from external aggression and oxidation, to combat the signs of skin ageing, to increase photoprotection, to lighten the skin and to improve skin hydration, without this amount being toxic.

The term "skin hydration" means the water content and distribution in the upper layers of the epidermis.

The term "improvement in skin hydration" means any improvement in changes in the external appearance of the skin caused by dehydration, such as dryness, tightness, and discomfort, whether related to internal or external factors, such as adverse environmental conditions.

The term "signs of skin ageing" means all modifications of the external appearance of the skin caused by ageing such as, for example, wrinkles and fine lines, cracks, bags under the eyes, dark circles, withering, loss of elasticity, firmness and/or tone of the skin, but also all internal modifications of the skin which do not systematically result in a modified external appearance such as, for example, thinning of the skin, or all internal degradation of the skin following environmental stresses such as pollution and solar radiation including UV rays.

The term "signs of skin ageing" also means pigmentary disorders such as senile lentigo or solar lentigo.

The term "external aggressions" means solar radiation, including visible light, UV and infrared radiation, pollution, which may come from the ambient atmosphere outside or inside the dwellings and includes particles of different sizes (10 μm for PM10, 2.5 μm for PM 2.5, or less than 100 nm for ultrafine particles) as well as several chemical elements (volatile organic compounds, polycyclic aromatic hydrocarbons, heavy metals, etc.).

The expression "improve the appearance of the skin" means that the skin texture appears finer, the luminosity more intense and the complexion more even.

The term "physiologically acceptable" means a medium or solvent suitable for contact with the outer layers of the skin or mucous membranes, without toxicity, irritation, undue allergic response or similar intolerance reaction, and proportionate to a reasonable benefit/risk ratio.

It is understood that the invention concerns mammals and more particularly humans.

Extraction Process

Classically described ribonucleic acid (RNA) extraction protocols use solvents unsuitable for cosmetic use (Zumbo, P. 2014 "Phenol-chloroform Extraction", 2014). These methods aim to obtain nucleic acids (RNA or DNA or small RNAs) that are completely purified, i.e. free of any other molecule of interest such as secondary metabolites, vitamins, sugars, peptides, etc. which may have beneficial effects on the skin and are therefore of cosmetic interest.

Also known is document FR2831168, which describes a process for obtaining a plant extract rich in nucleic acids (DNA and RNA). The process uses cellulolytic enzymes.

Also known from the prior art are patent documents EP1723958 and WO03101376, which describe a composition for topical application comprising a synthetic double-stranded RNA oligonucleotide with a length of 12 to 40 nucleotides of known sequence, having a siRNA (short interfering) function.

Also known is document FR1502361 (also published under the number WO2017084958), which describes a process for obtaining an aqueous extract of plants, enriched with low molecular weight ribonucleic acids (RNA), for preparing cosmetic compositions. The process uses EDTA at a concentration between 2 and 15 mM.

The use of phytic acid instead of EDTA has the following advantages: Unlike EDTA, phytic acid is a natural molecule found in the husk of seeds such as grains and legumes. Therefore, the use of phytic acid makes it possible to obtain a tea extract of 100% natural origin while maintaining a good extraction efficiency of the phytomolecules contained in the plant. The extraction efficiency of small RNAs as well as other compounds present in tea leaves, such as sugars, phenolic compounds, or organic acids like tartaric, malic or citric acid.

The invention thus firstly relates to an extraction process implemented for obtaining an aqueous extract of leaves from all types of tea of the species *Camellia sinensis.*

More particularly, the invention relates to an extraction process used to obtain an aqueous extract of leaves of fresh tea, pu'er tea, green tea or matcha tea.

The extraction process of the invention makes it possible to obtain an extract rich in phytomolecules of cosmetic interest, such as small RNAs of a length of at most 150 nucleotides, sugars, phenolic compounds, organic acids, theine and theanine, while avoiding the use of solvents which are not considered to be cosmetic solvents.

The process of the invention has a reduced impact on the environment.

The process of the invention can be applied to fresh tea leaves or to tea leaves that have been processed in various ways to meet the designation of matcha tea, green tea or pu'er tea.

In a first step a) of the process, the tea leaves are mixed with water. The water used is distilled water, demineralised water or water rich in mineral salts and/or trace elements. The preferred water used is distilled water.

Tea leaves can come in different forms: fresh, dry, whole or powdered.

Preferably, fresh or dry tea leaves are ground in water in step a). Grinding the tea leaves is a mechanical action that allows a better extraction. Grinding is unnecessary for tea leaves that are already in powder form, such as matcha tea, which is mixed directly with water.

In step a), the ratio of plant material to water is 3% to 20% w/w, more preferably 3% to 10%.

In a step b) phytic acid is added to the tea-water mixture of step a).

The extraction process continues with an alkaline lysis in the presence of phytic acid favouring the complete destructuration of the cell membranes as well as the nuclear membrane.

Phytic acid, which is an excellent chelating agent, will lead to the weakening and destruction of the pecto-cellulosic membranes of plant cells by sequestering, through complexation, divalent ions such as calcium ions which form ionic bridges between the pectin molecules surrounding the cellulose microfibrils. This has the consequence of promoting the release of the cell content during the extraction. The phytic acid treatment step in basic medium is essential to enrich the extract with low molecular weight RNA and also to ensure a better extraction yield of other phytomolecules of interest; namely sugars, phenolic compounds, organic acids as well as theine and theanine.

Phytic acid is a molecule naturally present in the husk of seeds such as grains and legumes. Phytic acid is present in the form of calcium or sometimes magnesium salts, and it plays an important role for the plant, for example, it is the main source of phosphorus.

Preferably, the phytic acid used is a phytic acid powder in the form of a sodium salt. Preferably it is used at a concentration of between 1 and 10 mM, preferably between 1 and 5 mM and even more preferably at a concentration of 3 mM.

The concentration of 3 mM is also optimal to have a better yield of other compounds of interest such as sugars, phenolic compounds, organic acids, theine and theanine.

In step c), the pH is adjusted to a basic value between 10 and 11 by adding sodium hydroxide (NaOH). During step c) it is essential that the pH is basic, between 10 and 11. Preferably, the pH is adjusted to a value between 10.3 and 10.8. Indeed, this level of pH, associated with the action of phytic acid, causes the destructuration of the cell membrane, including the nuclear membrane, the lysis of the plant cells and causes the denaturation of the DNA (the 2 strands of the double helix are separated).

Monitoring of the pH shows that it remains basic and stabilises between 9 and 11 at the end of step c).

The extraction step d) preferably lasts at least 1 hour, at a temperature between 40 and 80° C. Preferably, the step lasts 1 hour. Advantageously, the step is carried out at a temperature between 60° C. and 80° C. Even more preferably, the step is carried out at 80° C. During this step, the mixture is advantageously put under moderate agitation.

In a step e), the mixture obtained in d) is purified so as to eliminate the residual solid tea leaves and recover the soluble part which constitutes the aqueous crude extract according to the invention. Any method known to a person skilled in the art can be used to carry out these purification steps. Preferably, the mixture is filtered directly on filters with a porosity greater than or equal to 30 μm in order to collect the filtrate. The mixture obtained in c) can also be centrifuged at low speed, for example for at least 10 min at 4000 g, so as to sediment the residual plant material in the pellet and recover the aqueous crude extract in the supernatant.

In a step f), the pH is adjusted to a value between 6 and 8.

In a step g) powdered activated charcoal is added to the mixture. Preferably a mixture of two different types of charcoals is used, and even more preferably 0.25% (w/w) of each of the two types of activated charcoals is used in order to create a synergistic effect on the decoloration of the extract. Activated charcoals are selected for their ability to deplete the extract of polyphenols, which are mainly responsible for the colour of the extract. This step lasts preferably thirty minutes, at a temperature between 40 and 50° C. under agitation for an optimal result.

In a step h), the mixture obtained in step g) is purified by removing the charcoal particles using filters with a porosity greater than or equal to 30 μm so as to obtain a clarified filtrate.

In a step i), the filtrate obtained in step h) is brought into contact with powdered polyvinylpolypyrrolidones (PVPP) in order to remove a maximum of phenolic compounds, such as high molecular weight polyphenols, tannin types, contained in the mixture which would not have been retained by the charcoal treatment step and which contribute colour to the extract and would risk disturbing the stability of the extract. Preferably, a final concentration between 5 and 30 g/l of PVP is used. Even more preferably, a final concentration of 10 g/l of PVPP is used.

This step can last between 10 and 30 minutes, and preferably 10 minutes, at a temperature between 40 and 50° C. with agitation for an optimal result.

The process according to the invention and in particular steps g) to i) make it possible to obtain extracts which contain little or no polyphenols of the catechin, epicatechin or epigallocatechin type. Only extracts obtained from pu'er tea contain a low concentration of catechin. Thin-layer chromatography analyses showed that none of the tea extracts of the invention contained epicatechin or epigallocatechin.

In step j) the mixture obtained in step i) is clarified by removing the PVPP particles by using filters with a porosity greater than 25 μm, followed by filtration using a filter with a porosity of 0.8 μm.

In a step k), the pH of the mixture obtained in step j) is then adjusted to a value between 6 and 6.5. A crude extract according to the invention is then obtained.

The pH can be adjusted by adding a hydrochloric acid (HCl) solution or any other equivalent acid compatible with cosmetic use, such as citric acid. The pH adjustment step in step k) of the process according to the invention is an indispensable step to obtain a stable extract without precipitation of the phytochemicals of interest. Indeed, this pH is optimal for the maintenance in suspension of RNA of low molecular weight, as well as other phytomolecules of interest; such as sugars, phenolic compounds, organic acids, theine and theanine.

In fact, a pH below 6 can lead to the precipitation of nucleic acids in general, and thus to the precipitation of low molecular weight RNAs of a length of at most 150 nucleotides, or even to the precipitation of certain sugars, polyphenols and proteins. The step of adjusting the pH in step i) of the process according to the invention is an indispensable step to have an optimal stability of the extract.

The extract obtained in step k) can be diluted with a physiologically acceptable solvent for cosmetic use in order to stabilise the product and increase its preservation over time. A diluted extract is then obtained.

The extract is diluted to a dry weight between 4 and 20 g/kg, and its pH is adjusted to between 5.8 and 6.5, preferably between 6.0 and 6.5. This step makes it possible to improve the stability of the product over time.

The invention relates secondly to aqueous extracts of tea leaves obtained from fresh tea, pu'er tea, matcha tea or green tea, enriched with small RNAs of a length of at most 150 nucleotides, with sugars, with phenolic compounds, with organic acids, with theine and with theanine and free of DNA, obtainable by the above-described process. This extract does not contain DNA (deoxyribonucleic acid).

The invention also relates to aqueous extracts of tea leaves obtained from fresh tea, pu'er tea, matcha tea or green tea, enriched with small RNAs of a length of at most 150 nucleotides, with sugars, with phenolic compounds, with organic acids, with theine, and with theanine directly obtained by the process described above. This extract does not contain DNA (deoxyribonucleic acid).

By using the process of the invention according to steps a) to k), aqueous concentrated crude extracts of amber coloured to dark amber coloured tea are obtained having a dry weight of 5 to 30 g/kg, containing 0.5 to 10 g/kg of sugars, 0.050 to 2 g/kg organic acids, to 5 g/kg phenolic compounds including 0 to 200 mg/kg catechin, 0.020 to 2 g/kg theine and 0.020 to 2 g/kg of theanine and 50 to 350 mg/kg of low molecular weight RNA of a length of at most 150 nucleotides. Nevertheless, the tea leaves being subjected to various treatments, the extracts obtained can present a significant variability depending on factors such as the place or year of harvest, the season, the climatic conditions, the biotic stress, etc.

The extract thus obtained can then be diluted in a physiologically acceptable solvent for cosmetic use, so that the concentration of the extract is then adjusted to a dry weight between 4 and 20 g/kg.

Physiologically acceptable solvents include water, glycerol, ethanol, propanediol, butylene glycol and their natural versions, dipropylene glycol, ethoxylated or propoxylated diglycols, cyclic polyols or any mixture of these solvents. Ethanol, butylene glycol, propanediol and glycerin exist as synthetic solvents or as plant-derived solvents, the latter being described as the natural version.

Thus the extract obtained can be mixed with 30 to 50% of plant-derived butylene glycol, or 30 to 50% of plant-derived propanediol or 30 to 70% of plant-derived glycerin.

Preferably, the extract obtained by the process according to the invention is diluted in butylene glycol such that the diluted extract comprises a final butylene glycol concentration of 30% or 50%.

This so-called diluted extract has a dry weight of 4 to 20 g/kg, a concentration of 0.2 to 5 g/kg of sugars, 0.030 to 1 g/kg of organic acids, 0.030 to 3 g/kg of phenolic compounds including 0 to 120 mg/kg of catechin, 0.010 to 1 g/kg of theine and 0.010 to 1 g/kg of theanine, and 10 to 250 mg/kg of low molecular weight RNA of a length of at most 150 nucleotides.

A non-limiting example is a diluted green tea extract containing more particularly sugars at a concentration of 1.4 g/kg, organic acids at a content of 95.5 mg/kg, 32 mg/kg of phenolic compounds and 77 mg/kg of RNA of low molecular weight of a length of at most 150 nucleotides.

The extract of the invention thus comprises a wide range of phytomolecules that can exhibit beneficial effects on the skin, without presenting a risk of skin irritation or other health damage.

For example, sugars actively participate in the hydration of the upper layers of the epidermis, and in so doing, in the resistance to external aggressions, without presenting any undesirable effect. The tea extracts of the invention contain more particularly mono- and polysaccharides.

*Camellia sinensis* is a member of the Theaceae family, which produces theine, a powerful natural insecticide. Theine is also called caffeine or 1,3,7-trimethylxanthine or methyltheobromine. In addition to its recognised effects on the nervous and cardiovascular systems, theine also has beneficial effects on the skin, in particular on skin slackening.

The plant also produces theanine, a non-protein amino acid commonly found in tea leaves. Theanine is known for its relaxing activity on the brain allowing the reduction of mental and physical stress.

The tea extracts according to the invention also contain phenolic compounds, such as polyphenols, phenolic acids, flavonoids such as catechin, however this family of molecules has been partially removed by charcoal and PVPP treatment steps. This relative depletion of phenolic compounds increases the stability of the product over time and results in a non-phototoxic extract.

In a particular embodiment of the invention, the diluted aqueous extract according to the invention contains at most 1.5 g/kg of phenolic compounds, including at most 120 mg/kg of catechin.

In another particular embodiment of the invention, the diluted aqueous extract according to the invention contains at most 1.2 g/kg of phenolic compounds, including at most 30 mg/kg of catechin.

In another particular embodiment of the invention the diluted aqueous extract according to the invention contains at most 100 mg/kg of phenolic compounds and does not contain catechin.

In yet another particular embodiment of the invention, the diluted aqueous extract according to the invention contains at most 50 mg/kg of phenolic compounds and does not contain catechin.

In a particular embodiment of the invention the diluted aqueous extract according to the invention contains at most 3 g/kg of phenolic compounds and does not contain catechin.

The invention relates thirdly to a cosmetic composition comprising an effective amount of at least one aqueous tea extract selected from fresh tea, pu'er tea, matcha tea, green tea, or any mixture thereof, obtained according to the invention, as an active ingredient, and a physiologically acceptable medium.

Advantageously, the tea extracts according to the invention are added in a physiologically acceptable medium at a concentration of 0.05 to 5% by weight in relation to the total weight of the composition, preferably at a concentration of 0.1 to 2.5% by weight in relation to the total weight of the composition.

The composition usable according to the invention is formulated to be applied by any suitable route, in particular orally, or externally topically, and the formulation of the compositions will be adapted by a person skilled in the art.

Preferably, the compositions according to the invention are in a form suitable for topical application. These compositions must therefore contain a physiologically acceptable medium, i.e., compatible with the skin and the appendages, without any risk of discomfort during their application and cover all suitable cosmetic forms.

The compositions for implementing the invention may in particular be in the form of an aqueous, hydroalcoholic or oily solution or gel, an oil-in-water, water-in-oil, or multiple emulsion; they may also be in the form of suspensions or powders suitable for application to the skin, mucous membranes, lips and/or hair.

These compositions may be more or less viscous and may also have the appearance of a cream, lotion, fluid, milk, serum, ointment, gel, paste, balm or foam. They can also be in solid form, such as a stick, or can be applied to the skin as an aerosol.

Examples of physiologically acceptable media commonly used in the field of application envisaged are adjuvants necessary for the formulation, such as solvents, thickeners, gelling agents, diluents, emulsifiers, antioxidants, colorants, sunscreens, self-tanning agents, pigments, fillers, preservatives, perfumes, odour absorbers, essential oils, vitamins, essential fatty acids, surfactants, film-forming polymers, esters, and vegetable oils or butters, etc.

In all cases, a person skilled in the art will ensure that these adjuvants and their proportions are chosen in such a way as not to impair the advantageous properties sought in the composition according to the invention. These additives may, for example, each correspond to 0.01 to 20% of the total weight of the composition. When the composition according to the invention is an emulsion, the fatty phase may represent from 2 to 90% by weight and preferably from 5 to 30% by weight in relation to the total weight of the composition. The emulsifiers and co-emulsifiers used in the composition are chosen from those classically used in the field under consideration. For example, they can be used in a proportion ranging from 0.3 to 30% by weight in relation to the total weight of the composition.

According to another advantageous embodiment of the invention, the aqueous tea extracts of the invention can be encapsulated or included in a cosmetic vector such as liposomes or any other nano capsule or microcapsule used in the cosmetic field or adsorbed on powdery organic polymers, mineral supports such as talcs and bentonites.

Advantageously, the composition according to the invention can comprise, in addition to the active ingredient according to the invention, at least one other active agent having cosmetic effects similar and/or complementary to those of the invention.

For example, the additional active agent(s) may be selected from: anti-ageing, firming, brightening, moisturising, draining, microcirculation promoting, exfoliating, desquamating, extracellular matrix stimulating, energy metabolism activating, antibacterial, antifungal, soothing, antiradical, anti-UV, anti-acne, anti-inflammatory, anaesthetic, warm feeling inducing, cool feeling inducing, and slimming agents.

Such additional active agents may be selected from the groups comprising:

vitamin A and in particular retinoic acid, retinol, retinol propionate, retinol palmitate;

vitamin B3 and more particularly niacinamide, tocopherol nicotinate;

vitamin B5, vitamin B6, vitamin B12, panthenol;

vitamin C, in particular ascorbic acid, ascorbyl glucoside, ascorbyl tetrapalmitate, magnesium and sodium ascorbyl phosphate;

vitamins E, F, H, K, PP, coenzyme Q10;

metalloproteinase inhibitors, or a TIMP activator;

DHEA, its precursors and derivatives;

amino acids such as arginine, ornithine, hydroxyproline, hydroxyproline dipalmitate, palmitoylglycine, hydroxylysine, methionine and its derivatives, N-acylated amino acid compounds;

natural or synthetic peptides, including di-, tri-, tetra-, penta- and hexapeptides and their lipophilic, isomeric and complexed derivatives with other species such as a metal ion (for example copper, zinc, manganese, magnesium, and others). Examples include the peptides commercially known under the names of MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01 ™ (patent FR2837098, ASHLAND®), PEPTIDE VINCI 02™ (patent FR2841781, ASHLAND®), ATPeptide™ (patent FR2846883, ASHLAND®) or the synthetic peptide of sequence Arg-Gly-Ser-NH2, marketed under the name ATPeptide™ by ASH LAND®;

*Artemia salina* extract, marketed as GP4G™ (FR2817748, ASHLAND®);

plant peptide extracts such as flax extracts (Lipigenin™, patent FR2956818, ASHLAND®), extracts of soy, spelt, grapevine, rapeseed, flax, rice, corn, pea;

yeast extracts, for example Dynagen™, (patent FR2951946, ASHLAND®) or Actopontine™ (patent FR2944526, ASHLAND®);

dehydroacetic acid (DHA);

phystosterols of synthetic or natural origin;

salicylic acid and its derivatives, alpha- and beta-hydroxy acids, silanols;

amino sugars, glucosamine, D-glucosamine, N-acetyl glucosamine, N-acetyl-D-glucosamine, mannosamine, N-acetyl mannosamine, galactosamine, N-acetyl galactosamine;

extracts of polyphenols, isoflavones, flavonoids, such as grape extracts, pine extracts, olive extracts;

lipids such as ceramides or phospholipids, oils of animal origin, such as squalene or squalane; vegetable oils, such as sweet almond, copra, castor, jojoba, olive, rapeseed, peanut, sunflower, wheat germ, corn germ, soybean, cotton, alfalfa, poppy, pumpkin, evening primrose, millet, barley, rye, safflower, passionflower, hazelnut, palm, apricot kernel, avocado, calendula; ethoxylated vegetable oils, shea butter, cocoa butter, babassu butter;

all UV screens and sunscreens;

cyclic AMP and its derivatives, adenylate cyclase activating agents and phosphodiesterase inhibiting agents, *Centella asiatica* extract, asiaticoside and asiatic acid, methyl xanthines, theophylline, theobromine, forskolin, esculin and esculoside, ACE inhibitors, Val-Trp peptide, neuropeptide Y inhibitor, enkephalin, *Ginkgo biloba* extract, dioscorea extract rutin, yerba mate extract, guarana extract, oligosaccharides, polysaccharides, carnitine, extract of ivy, extract of rockweed, hydrolysed extract of Prunella vulgaris, hydrolysed extract of *Celosia cristata*, extract of *Anogeissus leiocarpus*, extract of leaves of *Manihot utilissima*, palmitoylcarnitine, carnosine, taurine, extract of elderberry, extracts of algae such as extract of *Palmaria Palmata;* hyaluronic acid or sodium hyaluronate and all its fractions and promoters;

menthol and menthyl lactate and other active ingredients with a fresh effect;

aloe vera, bisabolol, allantoin and other active ingredients with a soothing effect;

vanillyl butyl ether and other active ingredients with a heating effect;

benzoyl peroxide and other anti-acne active ingredients.

The invention relates fourthly to the cosmetic use of a composition comprising the tea extracts of the invention, originating from fresh tea, pu'er tea, matcha tea or green tea, or any mixture thereof, for the care of the skin, the scalp and the appendages, and more particularly to protect the skin from external aggression and oxidation, to fight against the signs of skin ageing, to increase photoprotection, to lighten the skin, and to improve skin hydration.

In a particular embodiment, the invention also relates to the cosmetic use of a composition comprising the tea extracts of the invention obtained from fresh tea, matcha tea or green tea, or any mixture thereof, for the care of the skin, the scalp and the appendages, and more particularly to protect the skin from external aggression and oxidation, to fight against the signs of skin ageing, to increase photoprotection, to lighten the skin, and to improve skin hydration.

The skin is an organ composed of several layers (dermis, epidermis and stratum corneum), which covers the entire surface of the body and ensures protective functions with respect to external, sensory, immune, metabolic and thermoregulatory aggressions or even barrier functions limiting dehydration.

In particular, the stratum corneum acts as a protective physical barrier, commonly referred to as the "skin barrier function". This function is of major importance in tissue homeostasis and protection from the external environment.

The appearance of the skin can be modified by internal alterations (intrinsic ageing, diseases and hormonal changes such as pregnancy) or external factors (environmental factors, such as pollution, sunlight, pathogens, temperature variations, etc.). All these alterations affect not only the skin, but also the keratinous appendages such as body hair, eyelashes, eyebrows, nails and head hair.

EXAMPLES

By way of illustration, examples of embodiments of the process according to the invention are described below.

Example 1: Preparation of Extracts of Fresh Tea, Pu'Er Tea, Matcha Tea or Green Tea (*Camellia sinensis*), Enriched with Small RNA According to the Process of the Invention In a first step a) to manufacture the extract, matcha tea (Japanese green tea in powder form), pu'er tea (tea originating from Yunnan in the form of compressed whole leaves), green tea (tea in the form of dried leaves originating from China) and fresh tea (leaves directly collected from a tree) all from the species *Camellia sinensis* were used.

The green tea or pu'er tea is weighed to represent 3% of the raw material involved in the process, or 30 g per 1 kg. The amount of distilled water added is 968 g.

The fresh tea is weighed to represent 6% of the raw material involved, or 60 g per 1 kg due to the water content representing half of the fresh weight of the leaves. The amount of distilled water added is 938 g.

The tea leaves and water mixture are ground in a blender to allow for better extraction of phytocompounds due to a larger exchange surface between the solid material, the tea, and the aqueous extraction solution.

Matcha tea, the dried leaves of which are already in powder form, is added directly to a mixture of 968 g of distilled water and 2 g/l or 3 mM of phytic acid homogenised beforehand.

In a step b), phytic acid at 2 g/l (i.e., 3 mM final) is added to the water and ground tea leaf mixtures (except for the matcha tea).

In a step c), the pH is adjusted to 10.5 for optimal extraction and to allow enrichment of the extract with low molecular weight RNA as well as with various phytomolecules.

In a step d) the mixture is heated for 1 h at 80° C. with moderate stirring.

In a step e) the mixture is filtered through filters with a porosity of 30 μm, to separate the solid matter from the filtrate. Three sequential filtrations are then carried out using filters of decreasing porosity in order to clarify the plant extract until a filtration at 3 μm of porosity.

Step f) The pH of the filtrate collected in step e) averages above 9 and is adjusted to between 6 and 8 to achieve an optimal pH for the subsequent activated charcoal treatment.

Step g) A treatment with a duo of activated charcoals is carried out in order to decolorise the extract by removing polyphenols in particular. 2.5 g of each type of charcoal per litre of extract are added. The treatment time is thirty minutes at a temperature between 40 and 50° C.

Step h): The charcoals are removed by passing the extract through filters with a porosity of 30 μm.

In step i) a second decoloration treatment of the filtrate obtained in g) is carried out by adding powdered polyvinylpolypyrrolidone (PVPP). 10 g/l of PVPP are added to the extract to remove some of the tannins contained in the extract. The treatment time is 10 minutes at a temperature between 40 and 50° C.

In step j), sequential filtrations on filters of decreasing porosity are then carried out to remove the PVPP from the vegetable extract; a first filtration of 30 μm makes it possible to retain the PVPP followed by successive filtrations up to a porosity of 0.8 μm in order to clarify the extract.

In step k) the pH is checked and then adjusted to a value between 6 and 6.5 with a citric acid or hydrochloric acid solution.

Aqueous crude extracts with dry weights between 5 and 30 g/kg are obtained.

The extract obtained in step k) is diluted with 30% butylene glycol. This solvent, which is physiologically acceptable for cosmetic use, makes it possible to stabilise the product, increasing its preservation over time. A diluted extract is then obtained, and the pH is adjusted to between 6.0 and 6.5.

The resulting diluted extract has a dry weight of between 4 and 20 g/kg.

The tea extracts thus obtained according to the process described in this example are referred to as PSR (Plant small RNA) tea in the tables or figures presented in the invention.

Example 2: Preparation of Tea (*Camellia sinensis*) Extracts by a so-Called Conventional Extraction Method For the purpose of comparison, tea extracts obtained by a so-called conventional or classical extraction were made.

This extraction process was chosen because it is optimal for extracting different types of phenolic compounds and other polar molecules such as sugars and amino acids, making it a good reference process for performing comparisons with the process of the invention applied in Example 1.

In a first step to manufacture 1 kg of extract, the same teas as in Example 1 were used: matcha tea (Japanese green tea in powder form), pu'er tea (tea originating from Yunnan in the form of compressed whole leaves), green tea (tea in the form of dried leaves originating from China) and fresh tea (leaves directly collected from a tree) all from the species *Camellia sinensis.*

The leaves of dried or powdered teas such as matcha, pu'er and green tea are weighed to represent 3% of the raw material used in the process, i.e., 30 g for 1 kg, to which 970 g of distilled water are mixed.

The leaves of fresh teas, which represent 6% of the raw material used, i.e., 60 g for 1 kg, due to their natural content of water are mixed with 940 g of distilled water. A grinding step was applied for fresh tea, green tea and pu'er tea. The extraction pH is not adjusted and is between 5 and 7.

The mixture is then heated for 1 h at 45° C. with stirring.

The mixture is then filtered through filters with a porosity of 30 μm, to separate the solid matter from the filtrate. Sequential filtrations are then carried out using filters of decreasing porosity in order to clarify the plant extract until a filtration at 1 μm of porosity.

At the end of this step, a charcoal treatment is carried out in order to decolorise the extract by removing polyphenols in particular. 2.5 g of each charcoal per litre of extract are added. The treatment time is thirty minutes at a temperature between 40 and 50° C. and a pH between 6 and 8. A 30 μm filtration is performed to remove the charcoal from the extract.

Then a second decoloration treatment is performed by adding powdered polyvinylpolypyrrolidone (PVPP). 10 g/l are added to the extract to remove some of the tannins contained in the extract. The treatment time is 10 minutes at a temperature between 40 and 50° C. Sequential filtrations on filters of decreasing porosity are then carried out in order to clarify the plant extract until a filtration at 0.2 μm.

The pH is checked and then adjusted to between 6 and 6.5 with a citric acid or hydrochloric acid or soda solution.

Aqueous crude extracts with dry weights between 1 and 5 g/kg are obtained. The process implemented in this Example 2 is intended to prepare a control extract to obtain comparative analytical data in relation the different tea extracts obtained by the process of the invention. The results obtained are illustrated in the figures and in the text of the application.

Example 3: Characteristics of the Tea Extracts Obtained According to Example 1

The crude extract of fresh tea made from fresh leaves directly harvested from the tree has a dry weight of 6.5 g/kg. The physicochemical analysis shows that the extract obtained has a concentration of 2 g/kg of total sugars, 120 g/kg of total organic acids, 31 mg/kg of total phenolic compounds and 120 mg/kg of low molecular weight RNA of a length of at most 150 nucleotides.

The extract is then diluted with a cosmetic solvent that is physiologically acceptable and makes it possible to ensure better stability and preservation of the extract over time; the amount of solvent can range from 30 to 70%.

The dilution is carried out with plant-derived butylene glycol to obtain a final concentration of 30% butylene glycol and 70% tea extract. The extract thus diluted has a dry weight of 4.3 g/kg and has a concentration of 1.4 g/kg of total sugars, 83 mg/kg of total organic acids, 48 mg/kg of total phenolic compounds and 74 mg/kg of RNA of low molecular weight of a length of at most 150 nucleotides.

The crude extract of green tea made from dried leaves originating from China has a dry weight of 10.2 g/kg. The physicochemical analysis shows that the extract obtained has a concentration of 1.5 g/kg of total sugars, 137 mg/kg of total organic acids, 1.3 g/kg of total phenolic compounds and 110 mg/kg of low molecular weight RNA of a length of at most 150 nucleotides.

The extract is then diluted with a cosmetic solvent that is physiologically acceptable and makes it possible to ensure better stability and preservation of the extract over time; the amount of solvent can range from 30 to 70%.

The dilution is carried out with plant-derived butylene glycol to obtain a final concentration of 30% butylene glycol and 70% tea extract. The extract thus diluted has a dry weight of 7.1 g/kg and has a concentration of 1.1 g/kg of total sugars, 96 mg/kg of total organic acids, 931 mg/kg of total phenolic compounds and 77 mg/kg of RNA of low molecular weight of a length of at most 150 nucleotides.

The crude extract of matcha tea prepared from crushed leaves originating from Japan has a dry weight of 14.2 g/kg. The physicochemical analysis shows that the extract obtained has a concentration of 2.4 g/kg of total sugars, 179 mg/kg of total organic acids, 2 g/kg of total phenolic compounds and 87 mg/kg of low molecular weight RNA of a length of at most 150 nucleotides.

The extract is then diluted with a cosmetic solvent that is physiologically acceptable and makes it possible to ensure better stability and preservation of the extract over time; the amount of solvent can range from 30 to 70%.

The dilution is carried out with plant-derived butylene glycol to obtain a final concentration of 30% butylene glycol and 70% tea extract. The extract thus diluted has a dry weight of 10.2 g/kg and has a concentration of 1.7 g/kg of total sugars, 125 mg/kg of total organic acids, 1420 mg/kg of total phenolic compounds and 61 mg/kg of RNA of low molecular weight of a length of at most 150 nucleotides.

The crude extract of pu'er tea made from compressed whole leaves originating from Yunnan has a dry weight of 13.8 g/kg. The physicochemical analysis shows that the extract obtained has a concentration of 3.3 g/kg of total sugars, 137 mg/kg of total organic acids, 193 mg/kg of total phenolic compounds and 250 mg/kg of low molecular weight RNA of a length of at most 150 nucleotides.

The extract is then diluted with a cosmetic solvent that is physiologically acceptable and makes it possible to ensure better stability and preservation of the extract over time; the amount of solvent can range from 30 to 70%.

The dilution is carried out with plant-derived butylene glycol to obtain a final concentration of 30% butylene glycol and 70% tea extract. The extract thus diluted has a dry weight of 8 g/kg and has a concentration of 1.1 g/kg of total sugars, 137 mg/kg of total organic acids, 1176 mg/kg of total phenolic compounds and 177 mg/kg of RNA of low molecular weight of a length of at most 150 nucleotides.

Example 4: Quantification of the Different Components of the Diluted Tea Extracts Obtained in Examples 1 and 2

The dry weight of each type of extract, obtained according to the process of the invention or according to a conventional process, was measured. The dry weight represents the weight of the extract after water and volatile compounds have evaporated after 12 h of steaming at 105° C.

The dry extracts of the various tea extracts obtained by the process according to the invention have a higher dry weight than the tea extracts obtained by conventional extraction. The extraction yield is therefore higher when the process of Example 1 is applied to extract the different types of tea; see Table 1.

TABLE 1

| | PSR fresh tea extract | Conventional fresh tea extract | PSR green tea extract | Conventional green tea extract | PSR matcha tea extract | Conventional matcha tea extract | PSR pu'er tea extract | Conventional pu'er tea extract |
|---|---|---|---|---|---|---|---|---|
| Dry weight (g/kg) | 4.5 | 1 | 7.1 | 2.3 | 10 | 3.1 | 8 | 3.6 |
| Extraction yield (%) | 15 | 3.3 | 23.7 | 7.7 | 33.3 | 10.3 | 46 | 24 |

The total sugar content in the different tea extracts obtained by the process of the invention versus the extracts obtained by the conventional process was determined by spectrophotometric assay derived from an adaptation of the assay described by Dubois et al. (1956) (Dubois et al., "Colorimetric method for the determination of sugars and related substances", Anal. Chem, 1956, 28 (3), 350-356). This analysis consists of dissolving the raw material in concentrated sulfuric acid and then reacting with phenol to form a coloured complex. The absorbance of the complex is read on the spectrophotometer at 490 nm. The sugar content is determined using a standard glucose curve.

The analysis shows the highest concentration of sugars extracted by the process described in the invention for all types of tea, fresh, green, matcha, pu'er tea compared to a conventional extraction process, see [FIG. 1].

The total polyphenol content of the tea extracts according to the invention versus the conventional tea extracts was determined by the Folin-Ciocalteu spectrophotometric assay method (Singleton et al, Analysis of total phenols and other oxidative and antioxidant substrates using the Folin-Ciocalteu reagent, 1999, 299: 152). The polyphenol type compounds present in the sample react with the Folin-Ciocalteu reagent; the oxidation of the reagent gives a blue colour. The absorbance of the sample is read on the spectrophotometer at 760 nm. The total polyphenol concentration is expressed as gallic acid equivalents using a gallic acid standard curve. The analysis shows the highest concentration of polyphenol extracted by the process described in the invention for all types of tea, fresh, green, matcha and pu'er tea compared to a conventional extraction process, see [FIG. 2].

Characterisation and quantification of the organic acids contained in the extracts of teas according to the invention versus the extracts of conventional teas was performed. A high-performance liquid chromatographic analysis, coupled with a mass detector was used. All samples were separated on an EC 150/4.6 Nucleoshell RP 18plus-5 μm column (150×4.6 mm) (Macherey Nagel: 763236.46) by an Agilent 1260 HPLC system (Agilent Technologies). The flow rate was 0.3 ml/min. The mobile phase consisted of a solution of 0.01% formic acid (HCOOH) (A) and acetonitrile (B). The gradient program facilitated elution as described in Table 2.

TABLE 2

| Time (min) | A Water/0.01% HCOOH (%) | B Acetonitrile (ACN) (%) |
|---|---|---|
| 0 | 100 | 0 |
| 9 | 100 | 0 |
| 13 | 5 | 95 |
| 14 | 5 | 95 |
| 15 | 100 | 0 |
| 20 | 100 | 0 |

The column temperature was maintained at 25° C. and the injection volume was 5 μL. Detection was performed by an ACQUITY Qda mass spectrometer detector (WATERS) with a negative mode electrospray ion source. The source was set at a capillary voltage of 0.8 kV and a probe temperature of 600° C. M/z and cone voltage were targeted for each compound as described in Table 3.

TABLE 3

| Compounds | Mass (m/z) | Cone voltage (V) |
|---|---|---|
| Tartaric acid | 149.0 | 10 |
| Malic acid | 132.9 | 3 |
| Citric acid | 191.0 | 10 |
| Lactic acid | 88.9 | 5 |
| Succinic acid | 116.95 | 15 |
| Uronic acid | 193 | 10 |

Identification of organic acids was performed by comparing the retention times and mass spectral peaks of the sample with a standard. Quantitative estimation of organic acids was performed on the basis of chromatographic peak areas compared to the areas of the standards.

HPLC-MS analysis to quantify and identify the organic acids contained in the different tea extracts obtained according to Examples 1 and 2 shows that the PSR tea extracts and the conventional extracts contain different types of organic acids, mainly citric, lactic, malic and succinic acid, as shown in Table 4. Tartaric acid and uronic acids were not detected in either the PSR tea extracts or in the conventional extracts.

TABLE 4

| Type of extracts | Citric acid | Lactic acid | Succinic acid | Malic acid | Tartaric acid | Uronic acids |
|---|---|---|---|---|---|---|
| | mg/kg | | | | | |
| PSR fresh tea | 39.0 | 7.7 | <LQ | 36.7 | nd | nd |
| conventional fresh tea | 10.2 | 4.4 | nd | nd | nd | nd |
| PSR green tea | 35.6 | 20.1 | 3.4 | 36.4 | nd | nd |
| conventional green tea | 29.5 | 2.9 | 2.2 | 33.5 | nd | nd |
| PSR matcha tea | 65.8 | 9.0 | 4.2 | 46.2 | nd | nd |
| conventional matcha tea | 62.3 | 6.1 | 6.6 | 35.7 | nd | nd |
| PSR pu'er tea | 77.1 | 8.1 | 5.1 | 46.5 | nd | nd |
| conventional pu'er tea | 66.8 | nd | 4.5 | 38.7 | nd | nd |

LQ: limit of quantification;
nd: not detected

The analysis also shows that these organic acids are extracted to a greater extent by the process of the invention than by conventional extraction as shown in [FIG. 3].

The characterisation of theanine contained in the tea extracts according to the invention versus conventional tea extracts was determined. Tea leaves contain this unique amino acid, which accounts for 50% of the total amount of amino acids in tea. It is a non-protein amino acid. A high-performance liquid chromatographic analysis, coupled with a UV detector was used. All samples were separated by a 250 mm×4.6 mm×5 um Uptisphere C18-2 column (Interchim) by an Agilent 1200 HPLC system (Agilent Technologies). The flow rate was 0.4 ml/min. The mobile phase consisted of 0.1% phosphoric acid (H3PO4) in aqueous solution (A) and acetonitrile (ACN) (B). Elution was facilitated by the gradient program as follows, see Table 5:

TABLE 5

| Time (min) | A Water/0.1% H3PO4 (%) | B ACN (%) |
|---|---|---|
| 0 | 100 | 0 |
| 8 | 100 | 0 |
| 10 | 50 | 95 |
| 15 | 5 | 95 |
| 16 | 100 | 0 |

The temperature of the column was maintained at 30° C. The injection volume was 5 μL and the detection wavelength was set at 196 nm and 210 nm using a UV detector. The theanine standard was purchased from Sigma-Aldrich. Identification of theanine was performed by comparing the retention time and UV spectral peak of the sample with a standard. Quantitative estimation of theanine was performed on the basis of chromatographic peak area compared to the area of the standard.

The HPLC-UV analysis, which makes it possible to quantify and identify the theanine contained in the various tea extracts obtained according to the process of the invention or according to a so-called conventional process, shows that the tea extracts obtained with the process of the invention contain theanine. However, less theanine is observed in the extracts obtained according to the invention than by conventional extraction as shown in [FIG. 4].

The characterisation of theine, which is the same molecule as caffeine, is an alkaloid present in large quantities in tea leaves. The theine content of the tea extracts according to the invention versus conventional tea extracts was also determined. All samples were separated on a 100 mm×4.6 mm×2.6 μm Uptisphere CS evolution C18-AQ column (Interchim) by an Agilent 1100 HPLC system (Agilent Technologies). The flow rate was 0.8 ml/min. The mobile phase consisted of 0.1% TFA (trifluoroacetic acids) in aqueous solution (A) and methanol (B). Elution was facilitated by the gradient program as follows, see Table 6:

TABLE 6

| Time (min) | A Water/0.1% TFA (%) | B Methanol (%) |
|---|---|---|
| 0 | 100 | 0 |
| 17.5 | 79 | 21 |
| 18.8 | 0 | 100 |
| 21 | 0 | 100 |
| 22 | 100 | 0 |

The temperature of the column was maintained at 25° C. The injection volume was 5 μL and the detection wavelength was set at 272 nm using a UV detector. The theine standard was purchased from Sigma-Aldrich. Identification of theine was performed by comparison of retention times and UV spectral peaks of the sample with an authentic standard. Quantitative estimation of theine was performed on the basis of chromatographic peak area compared to the area of the standard.

HPLC-UV analysis, which makes it possible to quantify and identify the theine contained in the various tea extracts obtained according to the process of the invention or according to a so-called conventional process, shows that all the types of tea extracts obtained with the process of the invention or according to a so-called conventional extraction contain theine. The results show that the extracts obtained by the process of the invention contain less theine than the tea extracts obtained by conventional extraction as shown in [FIG. 5].

Quantification of catechin was also performed. Catechin exists in the form of several stereoisomers due to the presence of two asymmetric carbons. In nature, the most frequent isomers are (+)-catechin and (−)-epicatechin. The other two enantiomers are much rarer and their presence seems to be related to enzymatic reactions or heat treatments. All samples were separated on a 100 mm×4.6 mm×2.6 μm Uptisphere CS evolution C18-AQ column (Interchim) by an Agilent 1100 HPLC system (Agilent Technologies). The flow rate was 0.8 ml/min. The mobile phase consisted of 0.1% TFA (trifluoroacetic acids) in aqueous solution (A) and methanol (B). Elution was facilitated by the gradient program as follows, see Table 7:

TABLE 7

| Time (min) | A Water/0.1% TFA (%) | B Methanol (%) |
|---|---|---|
| 0 | 100 | 0 |
| 4 | 100 | 0 |
| 20.5 | 65.9 | 54.1 |
| 27 | 32 | 68 |
| 29 | 5 | 95 |

The temperature of the column was maintained at 25° C. The injection volume was 20 μL and the detection wavelength was set to 255 nm, 280 nm, 290 nm and 324 nm using a UV detector. The catechin standard was purchased from Sigma-Aldrich. Identification of catechin was performed by comparing the retention times and UV spectral peaks of the sample with an authentic standard. Quantitative estimation of catechin was performed on the basis of the peak area of the sample concentrations relative to the area of the standard.

The HPLC-UV analysis, which makes it possible to quantify and identify the catechin contained in the various tea extracts obtained according to the process of the invention or according to a so-called conventional process, shows that the tea extracts obtained either by the process of the invention or by the conventional extraction contain little or no catechin-type polyphenols, as illustrated in [FIG. 4]. Only extracts obtained from pu'er tea contain some catechin. This absence or the low quantity of these molecules in the extracts is explained in particular by the implementation of the stages of treatment by the charcoals and by the PVPP, which removed this type of compound. These results were also confirmed and completed by the implementation of thin-layer chromatography, making it possible to visualise various molecules like catechin, epicatechin and epigallocatechin. None of the tea extracts, whether obtained by the process of the invention or by the conventional process, contained these molecules. This confirms the efficacy of the charcoal and PVPP treatment.

The quantification and measurement of the size of low molecular weight RNAs were carried out by a miniaturised electrophoresis technique on microfluidic chips specific to the analysis of nucleic acids such as low molecular weight RNAs (Bioanalyser 2100®, Agilent). This method makes it possible to determine the size and concentration of nucleic acids contained in an extract.

The results of the quantification by the Bioanalyser show that the tea extracts obtained by the process described in the present invention, allow the extraction of low molecular weight RNAs from the different types of tea as illustrated in Table 8. By contrast, no low molecular weight RNAs are detectable in conventional tea extracts (nd).

TABLE 8

| Type of extract | Small RNA (mg/kg) |
|---|---|
| PSR fresh tea | 74 |
| Conventional fresh tea | nd |
| PSR green tea | 77 |
| Conventional green tea | nd |
| PSR matcha tea | 61 |
| Conventional matcha tea | nd |
| PSR pu'er tea | 177 |
| Conventional pu'er tea | nd |

nd: not detected

Example 5: Evaluation of the Tea Extracts of Examples 1 and 2 in Respect of their Activity Towards the Inhibition of an Enzyme, Hyaluronidase, in an In Vitro Test Principle:

The objective of this test is to demonstrate the inhibitory power of the extracts from Examples 1 and 2 on the activity of an enzyme such as hyaluronidase via a test measuring turbidity. Hyaluronidase catalyses the degradation of hyaluronic acid (a glycosaminoglycan that is highly present in the skin's dermis and has moisturising and anti-ageing properties) into mono- or disaccharides as well as smaller hyaluronic acid fragments. Hyaluronic acid has the ability to react with an acidic albumin solution and thus form a haze that can be measured with a spectrophotometer at 600 nm. The inhibition of the enzyme activity is therefore measured by analysing the turbidity levels of the samples after having brought them into contact with the enzyme and its substrate.

Protocol:

The enzyme is incubated with the extracts obtained according to Examples 1 and 2, so as to represent a final concentration of 1% in the reaction mixture, for 20 minutes at a temperature of 37° C., in a buffer at pH7, ideal conditions for enzymatic equilibrium. The substrate of the enzyme, hyaluronic acid, is added to the mixture at a concentration of 0.3 mg/ml. The mixture is slowly homogenised and then incubated for exactly 45 minutes at 37° C. The hyaluronic acid remaining in the mixture is then brought into contact with an acidic albumin solution and homogenised. The time allowed for the reaction is 10 minutes before the transmittance is read at 600 nm on the spectrophotometer. The data are compared to those obtained with a negative inhibition control corresponding to the condition in which the enzyme has degraded 100% of the substrate, thus corresponding to 100% enzymatic activity.

Results:

The tea extracts prepared according to Example 1 show a percentage of hyaluronidase inhibition ranging from 67.9% (for the weakest, fresh tea) to about 80% (for the strongest, matcha and pu'er tea). The conventionally prepared tea extracts according to Example 2 show inhibition percentages ranging from 1.7% (weakest, green tea) to 57.7% (strongest, pu'er tea).

Conclusion:

Tests for evaluating the inhibitory effect of extracts on hyaluronidase activity in vitro have shown that the tea extracts prepared according to Example 1 exhibit significantly stronger inhibitory power of the enzyme than the extracts prepared according to Example 2 as shown in [FIG. 5].

Example 6

Evaluation of pu'er tea extract prepared according to Example 1 versus conventional pu'er tea extract prepared according to Example 2 on reactive oxygen species after application of monosodium glutamate stress on skin biopsies.

Principle:

The purpose of this study is to show the effect of pu'er tea extract prepared according to the invention on the reduction of reactive oxygen species generated by monosodium glutamate stress. Glutamate is known as an excitatory neurotransmitter of the central nervous system. In the skin, glutamate signalling occurs in nociceptive nerve endings and mechanoreceptor fibres.

Thioredoxin (TRX) is a class of small proteins involved in redox phenomena known to be present in all organisms. The primary function of the TRX-interacting protein (TXNIP) is to bind and inactivate TRX, resulting in increased accumulation of reactive oxygen species and apoptosis. TXNIP expression correlates robustly with the level of reactive oxygen species production.

Protocol:

Ex vivo human skin biopsies are cultured with a medium containing 100 mM monosodium glutamate and treated with either PBS (phosphate buffered saline) for the stressed control or with the pu'er tea extract prepared according to Example 1 at 0.5% (volume/volume dilution) and 1% (volume/volume dilution) or with the conventional pu'er tea extract prepared according to Example 2 at the same concentrations for 48 hours. As an unstressed control, skin biopsies are cultured with a conventional medium and treated with PBS. After treatment, the biopsies are fixed for histological analysis and embedded in paraffin. After deparaffinisation, antigenic sites are unmasked by microwave heating in citrate buffer pH=6 and saturation is done with 5% bovine serum albumin for 30 minutes. A rabbit monoclonal anti-TXNIP antibody is then applied at 1:100 for 1 hour and 30 minutes in a wet chamber. The sections are rinsed in a phosphate buffer and then incubated with Alexa 488® anti-rabbit secondary antibody for 1 hour in a humid chamber, protected from light. Finally, the sections are rinsed again in a phosphate buffer and then the slides are mounted for examination under the Eclipse E600 microscope (Nikon). The pictures are taken with the QImaging Retiga 2000R Fast1394 camera and analysed by the Q-Capture Pro 7 software (QImaging).

Results:

The application of monosodium glutamate stress resulted in an increase in reactive oxygen species (ROS) of +65% compared to unstressed skin biopsies. When skin biopsies were treated with the 0.5% (volume/volume dilution) and 1% (volume/volume dilution) extract of the invention, the ROS were highly significantly decreased by −28% and −29%, respectively, compared to untreated stressed explants. A conventional pu'er tea extract tested under the same conditions resulted in a smaller decrease of −7% and −18% respectively. The results are presented in [FIG. 6]. Mean+/−sem; n=10. Statistical analyses with Student's t-test, ns: not significant; ***: highly significant.

Conclusion:

[The pu'er tea extract prepared according to the invention showed antioxidant activity, directed against reactive oxygen species. This activity was found to be higher than that obtained with a conventional pu'er tea extract.

Example 7: Formula of a Rich Cream

TABLE 9

| Ingredients (Brand name) | INCI | % w/w |
|---|---|---|
| | Phase A | |
| Purified water | Aqua | Qsp 100 100 |
| Optiphen ™ Plus preservative | Phenoxyethanol (and) Caprylyl Glycol (and) Sorbic Acid | 1.50 |
| | Phase B | |
| Stabileze ™ QM polymer | PVM/MA Decadiene Crosspolymer | 0.15 |
| | Phase C | |
| ProLipid ™ 141 lamellar gel | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 5.00 |
| Ceraphyl ™ 494 ester | Isocetyl Stearate | 4.00 |
| Ceraphyl ™ SLK ester | Isodecyl Neopentanoate | 4.00 |
| Dowsil 580 Wax | Stearoxytrimethylsilane (and) Stearyl Alcohol | 2.00 |
| Emulsynt ™ GDL ester | Glyceryl Dilaurate | 3.00 |
| | Phase D | |
| Gransil DM-5 | Dimethicone (and) Polysilicone-11 | 3.00 |
| | Phase E | |
| Sodium hydroxide | Sodium Hydroxide | 0.04 |
| Purified water | Aqua | 0.50 |
| | Phase F | |
| fragrance | Perfume/Fragrance | 0.30 |
| | Phase G | |
| Extract according to example 1 | Butylene glycol (and) *Camellia Sinensis* Leaf Extract | 1.00 |
| Covabead Velvet 10 | Polymethyl Methacrylate | 1.00 |
| | Phase H | |
| Purified water | Aqua | 15.00 |
| Natrosol ™ Plus 330 HMHEC | Cetyl Hydroxyethylcellulose | 0.50 |

Preparation Process:

1. Homogenise phase A in the main vessel and start heating at 75-80° C.;
2. At 30° C., sprinkle into phase B and homogenise while heating;
3. In a separate beaker, prepare phase C, heat to 75-80° C. until homogeneous;
4. At 75° C., add phase C to the main vessel and homogenise for 10 minutes;
5. Allow temperature to cool and add phase D at 65° C. Mix well to homogenise for 10 minutes;
6. Pre-mix phase E before adding it to the main vessel;
7. Add phase E at 60° C. Mix well to homogenise for 10 minutes;
8. At 35° C., add phase F and mix well;
9. Pre-mix phase G before adding it to the main vessel;
10. Add phase G at 35° C. Mix well to homogenise;
11. In a separate beaker, prepare phase H: sprinkle Natrosol™ into water at room temperature and homogenise while heating to 60° C.;
12. Add phase H at 30° C. Mix well to homogenise;
13. Stop at 25° C.

The composition is thus in the form of a white butter-cream, with a pH between 4.90 and and a viscosity (DO) of 160,000-210,000 cps (Brookfield RVT/Spindle D/5 RPM/1 minute/25° C.).

Example 8: Formula of an Anti-Ageing Mask

TABLE 10

| Ingredients (Brand name) | INCI | % w/w |
|---|---|---|
| | Phase A | |
| Purified water | Aqua | Qsp 100 |
| Tetrasodium EDTA | Tetrasodium EDTA | 0.05 |
| | Phase B | |
| N-Hance ™ HP40S guar | Hydroxypropyl Guar | 0.10 |

TABLE 10-continued

| Ingredients (Brand name) INCI | | % w/w |
|---|---|---|
| Phase C | | |
| Lubrajel ™ DV Free hydrogel | Glycerin (and) Glyceryl Acrylate/Acrylic Acid Copolymer | 6.00 |
| Phase D | | |
| Si-Tec ™ GF 3096 silicone | Dimethicone (and) Dimethiconol | 12.00 |
| RapiThix ™ A-60 polymer | Sodium Polyacrylate (and) Hydrogenated Polydecene (and) Trideceth-6 | 2.40 |
| Phase E | | |
| Optiphen ™ Plus preservative | Phenoxyethanol (and) Caprylyl Glycol (and) Sorbic Acid | 1.50 |
| Phase F | | |
| Surfin* 96 | Alcohol Denat. | 3.50 |
| perfume | Perfume/Fragrance | 0.50 |
| Phase G | | |
| Extract according to example 1 | Water/Aqua (and) Butylene glycol (and) *Camellia Sinensis* Leaf Extract | 1.00 |
| Xirona Carribean Blue | Mica (and) CI 77891 (Titanium Dioxide) (and) Silica (and) Tin Oxide | 1.00 |

Preparation Process:

1. At 25° C., homogenise phase A in the main vessel;
2. At 25° C., sprinkle into phase B and mix well until homogeneous;
3. At 25° C., add phase C and mix well until homogeneous;
4. Pre-mix phase D in a separate beaker and add to the main vessel at 25° C.;
5. At 25° C., add phase E to the main vessel and mix well;
6. Pre-mix phase F and add it slowly. Mix well until homogeneous;
7. Pre-mix phase G in a separate beaker and add to the main vessel until homogeneous;
8. Stop at 25° C.

The composition is thus in the form of a creamy gel with glittering green effects, with a pH between 5.30 and 5.80 and a viscosity (DO) of 70,000-100,000 cps (Brookfield RVT/Spindle C/5 RPM/1 minute/25° C.).

Example 9: Formula of a Serum

TABLE 11

| Ingredients (Brand name) INCI | | % w/w |
|---|---|---|
| Phase A | | |
| Demineralised water | Aqua | 87.40 |
| Sodium Hyaluronate | Sodium Hyaluronate | 0.20 |
| RapiThix ™ A-60 polymer | Sodium Polyacrylate (and) Hydrogenated Polydecene (and) Trideceth-6 | 0.40 |
| Lubrajel ™ DV hydrogel | Glycerin (and) Glyceryl Acrylate/Acrylic Acid Copolymer (and) Propylene Glycol | 6.00 |
| Lubrajel ™ Oil hydrogel | Glycerin (and) Glyceryl Acrylate/Acrylic Acid Copolymer (and) Propylene Glycol (and) PVM/MA Copolymer | 1.00 |
| Wacker-Belsil* DM 100 | Dimethicone | 2.00 |
| Cyclopentasiloxane NF | Cyclopentasiloxane | 0.50 |
| Extract according to Example 1 | Water/Aqua (and) Butylenei glycol (and) *Camellia Sinensis* Leaf Extract | 1.00 |
| Optiphen ™ preservative | Phenoxyethanol (and) Caprylyl Glycol | 1.50 |

Preparation Process:

1. Add water to the main vessel and start mixing with a hi-lo propeller blade;
2. Add remaining ingredients, one at a time, stirring between each addition.

The composition is thus present in the form of a smooth, semi-opaque serum with a pH between 5.75 and 6.25 and a viscosity (D0) of 1,100-1,400 cps (Brookfield RVT/spindle 3/20 rpm/25° C./1 minute).

What is claimed is:

1. A process for obtaining an aqueous extract of tea leaves of the species *Camellia sinensis*, selected from fresh tea, pu'er tea, matcha tea or green tea, comprising:

a) bringing the tea leaves or tea powder into contact with water, and crushing the tea leaves;
b) adding phytic acid at a concentration between 1 and 10 mM to obtain a mixture;
c) adjusting the pH of the mixture to a value between 10 and 11;
d) keeping the mixture under agitation for at least one hour at a temperature between 4° and 80° C.;
e) purifying the mixture obtained in d) to eliminate residual solid plant material and collecting the resulting first filtrate;
f) adjusting the pH of the first filtrate to a value between 6 and 8;
g) treating the first filtrate with powdered activated charcoal;
h) filtering to remove the activated charcoal and collecting the resulting second filtrate;
i) treating the second filtrate with polyvinylpolypyrrolidones;
j) filtering to remove the polyvinylpolypyrrolidones and collecting the resulting third filtrate;
k) checking and readjusting the pH of the third filtrate, if necessary, to a value between 6 and 6.5, wherein adding phytic acid in b) under alkaline conditions causes lysis of plant cells and enrichment of the extract in low molecular weight ribonucleic acid.

2. The process according to claim 1, wherein in a), the tea leaves are brought into contact with water in a plant material/water ratio of 3% to 20% w/w.

3. The process according to claim 1, wherein in b), the phytic acid is at a concentration between 1 and 5 mM.

4. The process according to claim 1, wherein in e), at least one filtration is performed on filters with a porosity greater than or equal to 30 μm.

5. The process according to claim 1, wherein in j), sequential filtrations are carried out with filters of porosity greater than 25 μm, followed by filtration with a filter of porosity 0.8 μm.

6. The process according to claim 1, wherein after k), the extract is subsequently diluted in a physiologically acceptable solvent and its pH is adjusted to a value between 5.8 and 6.5, in order to obtain a diluted extract with a dry weight between 4 and 20 g/kg.

7. The process according to claim 6, wherein the physiologically acceptable solvent is selected from water, glycerol, ethanol, propanediol, butylene glycol, dipropylene glycol, ethoxylated or propoxylated diglycols, cyclic polyols, or any mixture of these solvents.

8. The process according to claim 3, wherein the concentration is between 1 and 3 mM.

* * * * *